United States Patent
Chodankar

(12) 
(10) Patent No.: US 11,767,281 B2
(45) Date of Patent: Sep. 26, 2023

(54) MANUFACTURING AND PURIFICATION TECHNOLOGY FOR HIGH PURITY PROPOFOL

(71) Applicant: Nandkumar Kashinath Chodankar, Panaji (IN)

(72) Inventor: Nandkumar Kashinath Chodankar, Panaji (IN)

( * ) Notice: Subject to any disclaimer, the term of this patent is extended or adjusted under 35 U.S.C. 154(b) by 0 days.

(21) Appl. No.: 17/428,975

(22) PCT Filed: Feb. 4, 2021

(86) PCT No.: PCT/IB2021/050889
§ 371 (c)(1),
(2) Date: Aug. 5, 2021

(87) PCT Pub. No.: WO2021/156776
PCT Pub. Date: Aug. 12, 2021

(65) Prior Publication Data
US 2023/0159420 A1    May 25, 2023

(30) Foreign Application Priority Data
Feb. 6, 2020 (IN) .............................. 202021005266

(51) Int. Cl.
| | | |
|---|---|---|
| C07C 37/76 | (2006.01) | |
| C07C 37/68 | (2006.01) | |
| C07C 37/50 | (2006.01) | |
| C07C 37/78 | (2006.01) | |

(52) U.S. Cl.
CPC .............. *C07C 37/76* (2013.01); *C07C 37/50* (2013.01); *C07C 37/685* (2013.01); *C07C 37/78* (2013.01)

(58) Field of Classification Search
CPC ....... C07C 37/78; C07C 37/685; C07C 37/76; C07C 37/50
See application file for complete search history.

(56) References Cited

U.S. PATENT DOCUMENTS

| | | | |
|---|---|---|---|
| 5,589,598 A | 12/1996 | Paiocchi | |
| 5,591,311 A * | 1/1997 | Ramachandran | C07C 37/72 568/756 |
| 5,696,300 A | 12/1997 | Bellani et al. | |
| 7,550,155 B2 * | 6/2009 | Zhang | A61K 31/56 424/486 |
| 8,664,452 B2 * | 3/2014 | Jain | C07C 37/11 568/716 |
| 8,962,696 B2 | 2/2015 | Harris et al. | |
| 2006/0052632 A1 * | 3/2006 | Ueno | C07C 51/15 562/406 |
| 2012/0158610 A1 | 6/2012 | Botvinick et al. | |

FOREIGN PATENT DOCUMENTS

| | | | | |
|---|---|---|---|---|
| CN | 106565424 B | | 4/2017 | |
| GB | 1 396 107 | * | 6/1975 | ............. C07C 39/06 |
| GB | 1396107 | | 6/1975 | |
| IN | 2424 | * | 11/2008 | |
| WO | WO 1996/001243 A1 | | 1/1996 | |
| WO | WO 2012/152665 A1 | | 11/2012 | |

OTHER PUBLICATIONS

Examination Report, Intellectual Property India Patent Office, dated May 2, 2022.
PCT International Search Report, dated May 24, 2021.
Written Opinion of the International Searching Authority, dated May 24, 2021.

* cited by examiner

*Primary Examiner* — Rosalynd A Keys
(74) *Attorney, Agent, or Firm* — Rajendra Gurudas Sardesai

(57) ABSTRACT

A process for manufacturing Pure Propofol with a purity of more than 99.90% is disclosed, said process comprising dissolving Crude Propofol in a solvent in which it is soluble to form a solution, treating the solution with aqueous alkali to form an aqueous alkali layer and a solvent layer, separating the aqueous alkali layer from the solvent layer using a phase separation technique, distilling off the solvent from the solvent layer, and distilling a residue of the solvent containing Propofol using steam or boiling water in a presence of dilute alkali and antioxidant like metabisulfite, under normal pressure or mild vacuum.

19 Claims, 5 Drawing Sheets

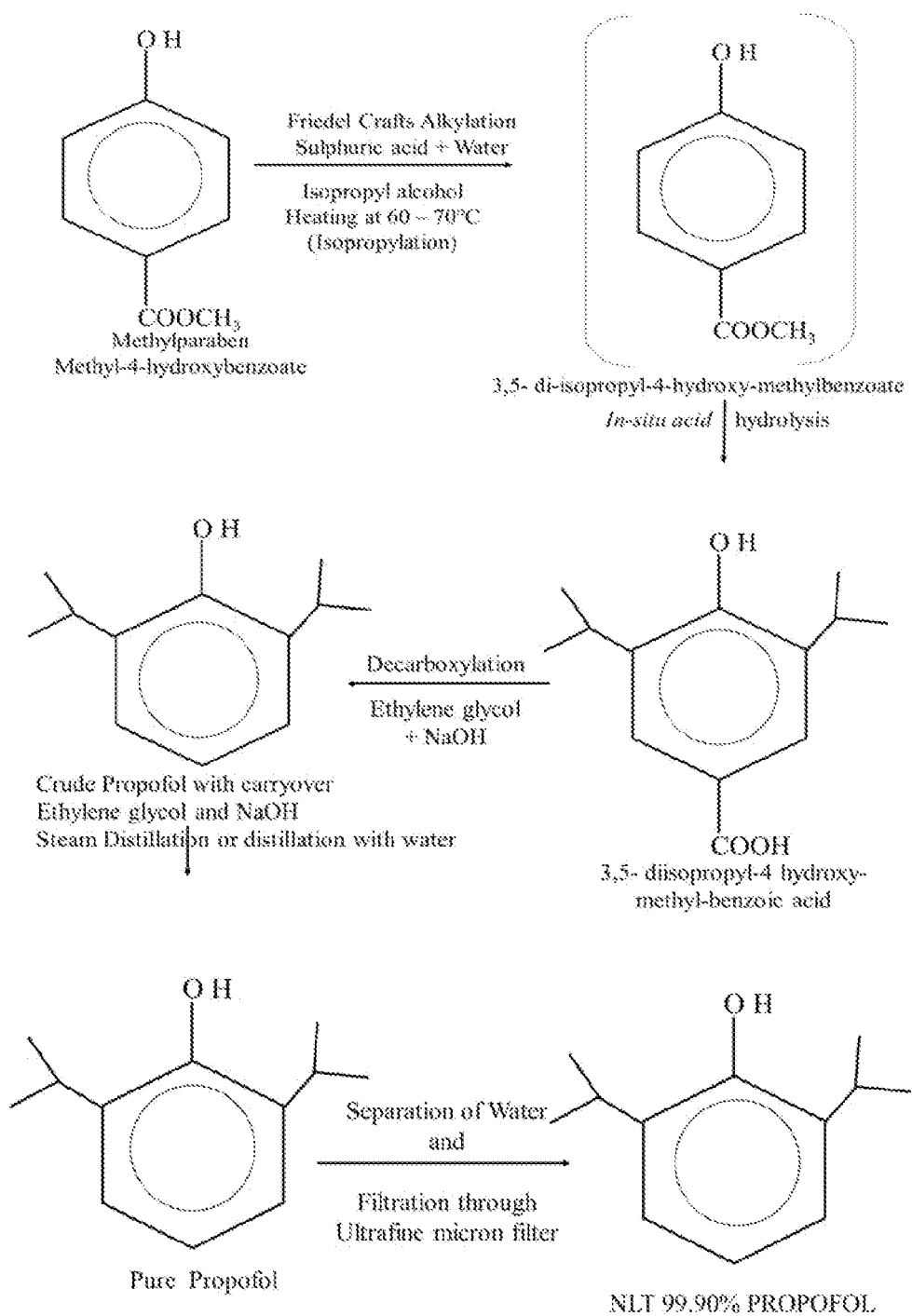
FIG. 1 Reaction scheme

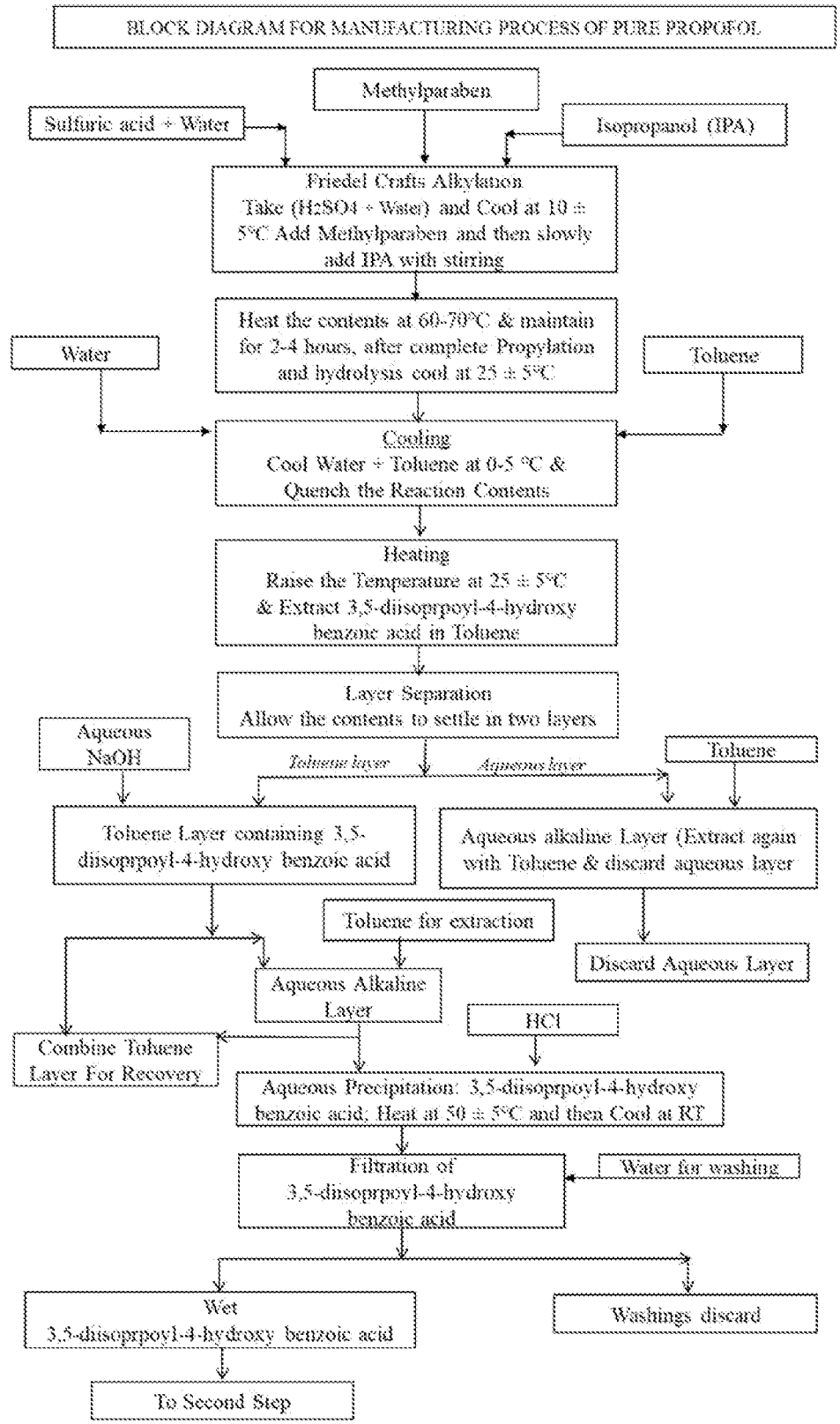
FIG. 2a: Step 1 of Manufacturing Process of Pure Propofol

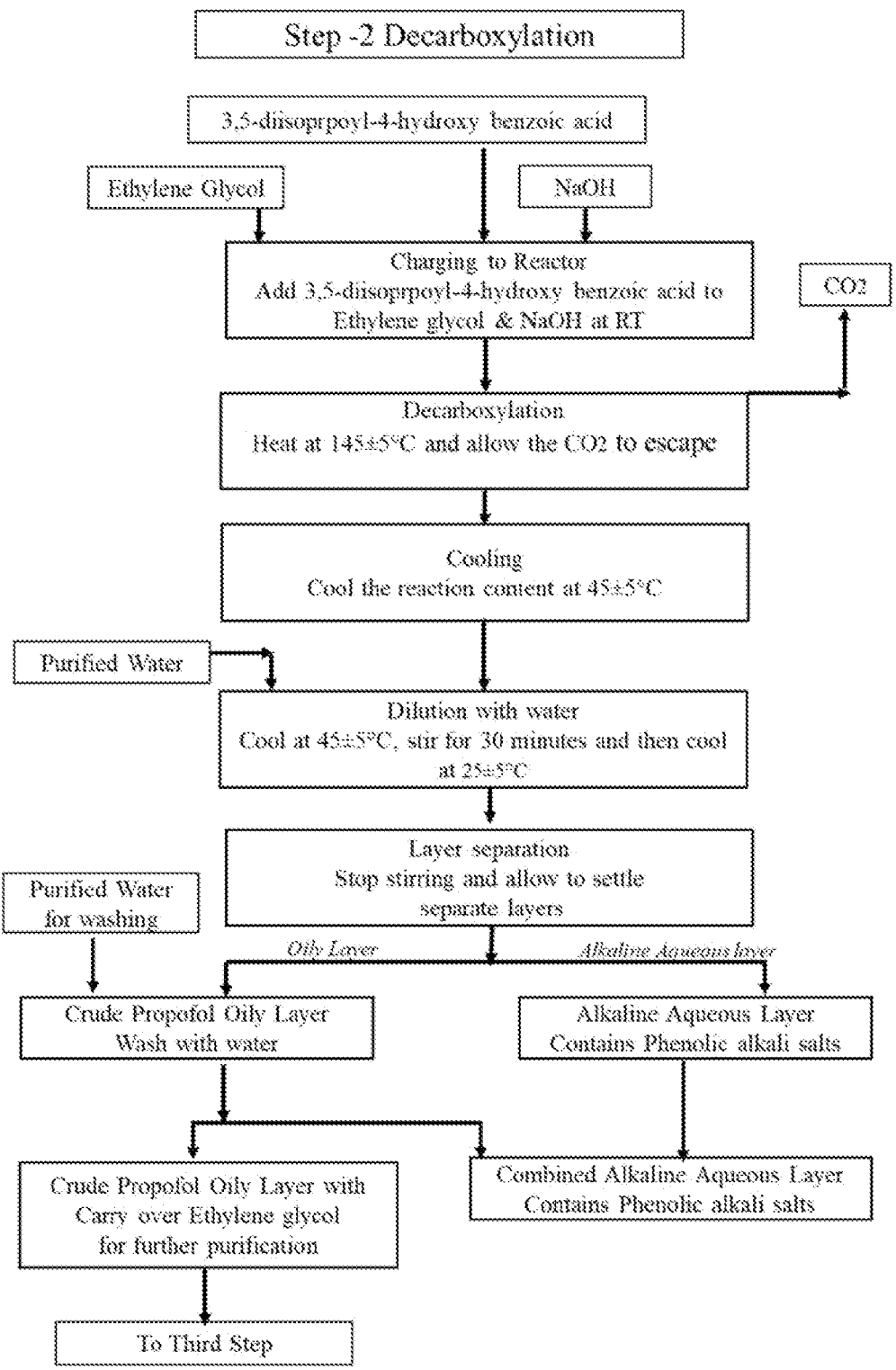
FIG. 2b : Step 2 of Manufacturing Process of Pure Propofol

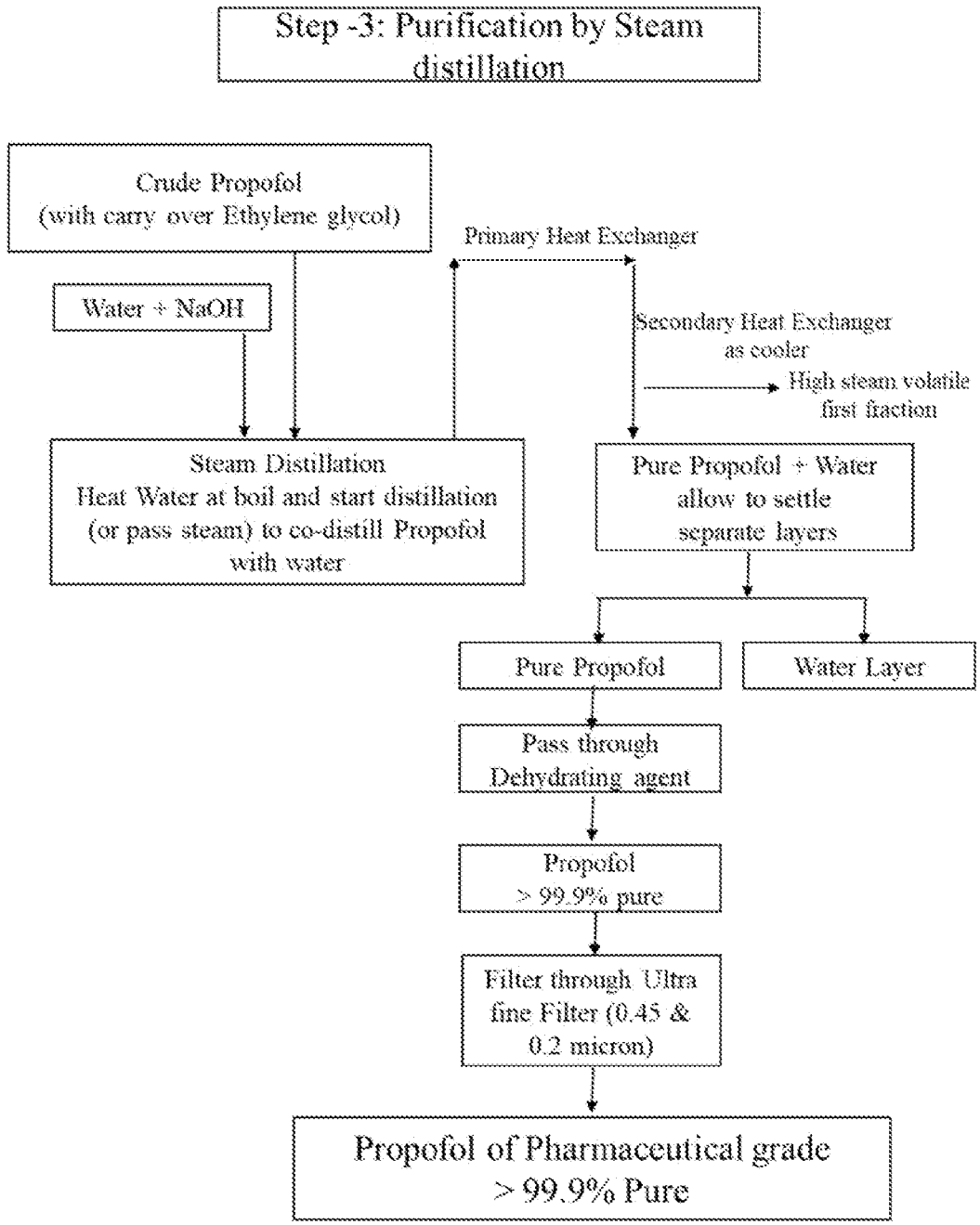
FIG. 2c: Step 3 of Manufacturing Process of Pure Propofol

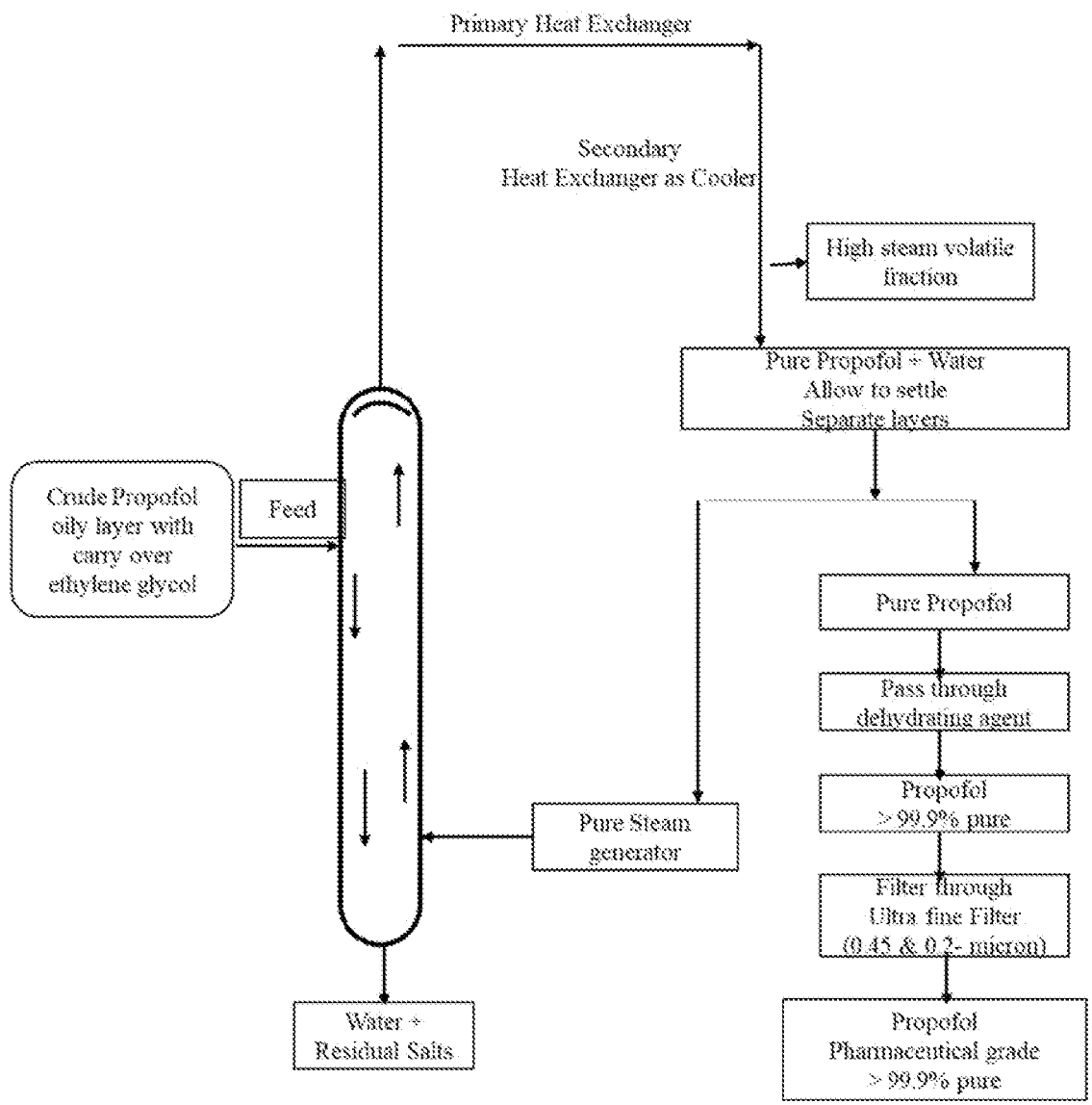
FIG. 2d: Schematic of Steam Distillation in Manufacturing Process of Pure Propofol

MANUFACTURING AND PURIFICATION TECHNOLOGY FOR HIGH PURITY PROPOFOL

TECHNICAL FIELD

The present disclosure generally pertains to a process for purification of 2,6-dialkylphenols, specifically of 2,6-diisopropylphenol commonly known as Propofol that is therapeutically used as an anaesthetic in medical practice. For example, the disclosure pertains to a process for the purification of Propofol so as to get a purity of more than 99.90%.

BACKGROUND OF THE INVENTION

Propofol is used during surgeries for sedation and an injectable grade with purity >99.90% is desired by the medical community. An embodiment of the present invention provides an economically feasible, industrial process for the manufacture of high purity injectable grade Propofol. An embodiment of the present invention relates to a process and novel strategy for purification of 2,6-diisopropylphenol (Propofol) and similar products.

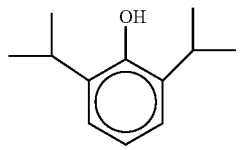

Propofol

Propofol is a sterile injectable drug that appears in the USP, EP and IP Monographs. Drug product is manufactured by using high purity drug substance 2,6-di-isopropylphenol commonly known as Propofol.

Propofol is used to put patients to sleep and keep them asleep during general anesthesia for surgery or other medical procedures. It is used in adults as well as children 2 months and older. Propofol is frequently used as a sedative, and has a rapid onset of action and a short recovery period. Propofol slows the activity of brain and nervous system. Propofol is also used to sedate a patient who is under critical care and needs a mechanical ventilator (breathing machine). Propofol is a hypnotic alkylphenol derivative. When formulated for intravenous induction of sedation and hypnosis during anaesthesia, Propofol facilitates inhibitory neurotransmission mediated by gamma-Aminobutyric acid (GABA). Propofol is associated with minimal respiratory depression and has a short half-life with a duration of action of 2 to 10 minutes.

Propofol is commonly used parenteral anesthetic agent in the United States, extensively used for minor and outpatient surgical procedures because of its rapid onset and reversal of action, and in intensive care units (ICUs) for maintaining coma. Propofol has been associated with rare instances of idiosyncratic acute liver injury; in addition, prolonged high dose Propofol therapy can cause the "Propofol infusion syndrome" which is marked by brady arrhythmias, metabolic acidosis, rhabdomyolysis, hyperlipidemia and an enlarged or fatty liver.

Friedel-Craft's alkylation of phenol using propylene gas in the presence of Lewis acid (LA) catalysts is a commonly used method for the synthesis of Propofol and is well documented in a number of publications and patents [Ecke, G. G., Kolka, A. J. U.S. Pat. No. 2,831,898 A, 1958. Firth, B. E., Rosen, T. J. U.S. Pat. No. 4,447,657, 1984. Akio, T., Yoshiaki, I., Hidekichi, H., Kiyoji, K., Takashi, K., Masanobu, M. EP 0169359A1, 1986. Ecke, G. G., Kolka, A. J. U.S. Pat. No. 3,271,314, 1966. Napolitano, J. P. U.S. Pat. No. 3,367,981 A, 1968. Goddard L. E. U.S. Pat. No. 3,766,276, 1973. Firth, B. E. U.S. Pat. No. 4,275,248, 1981, etc.]

A number of patents and published literature describe the manufacture of Propofol. U.S. Pat. No. 4,275,248; WO200034218; EP169359; U.S. Pat. Nos. 3,367,981; 3,271,314; 3,766,276; 2,831,898; 2,207,753; GB1318100; U.S. Pat. Nos. 4,391,998; 4,774,368; 5,589,598; 6,362,234; etc. EP 0511947, discloses purification of Propofol that is obtained by alkylation of phenol and purified by crystallization at −10 to −20° C. (melting point of Propofol is 18° C.). This patent also describes purification using non-polar solvents such as Petroleum ether or Hexane, where solvent residue is removed by distillation or evaporation and finally Propofol is obtained using fractional distillation under high vacuum.

Continuous separation of a mixture of Propofol with phenolic impurities and methanol is described in an U.S. Pat. No. 5,264,085. U.S. Pat. No. 5,705,039 describes the purification of impure 2,6-diisopropylphenol first using continuous distillation and then distilling pure Propofol under high vacuum.

Patent CN103360219A describes purification wherein 2,6-diisopropyl phenol is reacted with benzoyl chloride to generate 'benzoic acid-2,6-diisopropyl benzene ester', which is then purified to yield Propofol. The patent discloses that an adsorbent is added at the rectifying stage, so that impurities with similar chemical structures and boiling points are effectively removed; the content of a single impurity in the product is not higher than 0.01%; the total impurity is not higher than 0.05%.

CN105601477A describes purification of Propofol wherein crude Propofol is purified with three-stage distillation method; the crude Propofol enters feeding tank protected by nitrogen and is charged into first-stage film distillation system through pump; then the product is fed to second-stage molecular distillation system and low boiling point impurities are removed; finally, the processed product is charged into third-stage molecular distiller through a pump, high-boiling-point impurities are separated, and the colourless or yellowish high-purity Propofol is obtained.

In another prior art disclosure, after completion of the reaction, the final product is isolated and purified by high-vacuum distillation. Alkylation of phenol using propylene gas at high pressure and high temperature is reported. Several impurities like 2,4-diisopropyl and 2,4,6-triisopropyl phenol are the major side products along with the corresponding Isopropyl ether. All these impurities need to be controlled at a limit of NMT 0.05% or less in the final API for it to be pharmaceutically acceptable. In another prior art disclosure, isopropanol was used as the propylating agent instead of direct propylene gas. In this method propylene is generated in situ using IPA and strong acid like sulfuric acid and catalysts like Aluminoslicate [See Baltalksne, A. E.; Zitsmanis, A. H. SU 443019, 1974. Jain, K. P., Edaki, D. U., Minhas H. S., Minhas G. S. WO/2011/161687 A1, 2011. Wu, M. U.S. Pat. No. 4,391,998, 1983].

Another method is to use of protected phenol, where 4-chloro or 4-carboxylic acid substituted phenol is used as starting material along with Isopropanol in sulfuric acid, followed by removal of the 4-substituent to give Propofol [Baltalksne, A. E.; Zitsmanis, A. H. SU 443019, 1974. Jain, K. P., Edaki, D. U., Minhas H. S., Minhas G. S. WO/2011/161687 A1, 2011. Wu, M. U.S. Pat. No. 4,391,998, 1983. Tsutsumi, S.; Yoshizawa, T.; Koyama, K. Nippon Kagaku Zasshi 1956, 77, 737-738. Paiocchi, M. U.S. Pat. No. 5,589,598, 1996. Nieminen, K., Essen, P. U.S. Pat. No. 5,175,376, 1992. Keller, S., Schlegel, J. WO/2012/152665 A1, 2012.] The final purification is carried out by high-vacuum distillation to get highly pure Propofol. Since the para position is blocked, related impurities such as 2,4-isopropyl and 2,4,6-triisopropyl derivatives are avoided. In this approach, intermediate is purified before converting to crude Propofol using either de-chlorination by hydrogenation or de-carboxylation before vacuum distillation for final purification.

It is reported in the literature that 4-hydroxybenzoic acid is used as starting material for alkylation with isopropyl alcohol in sulfuric acid. In that method 2,6-diisopropyl-4-hydroxy benzoic acid gets formed, which is extracted in toluene either in presence of an acid or the impurities are extracted in toluene under alkaline condition. The decarboxylation is carried out using solvents like monoethylene glycol or ethoxyethanol at high temperature. At the end of decarboxylation, crude Propofol is isolated by extracting into toluene. The advantage is Propofol does not form sodium salt under the conditions, but all other acidic impurities form sodium salt and thus do not get extracted in toluene. The toluene containing Crude Propofol is distilled to recover toluene and then vacuum distilled to obtain pure Propofol. [Chen, J.; Chen, X.; Bois-Choussy, M.; Zhu, J. J. Am. Chem. Soc. 2006, 128, 87-89. Lau, S.; Keay, B. Can. J. Chem. 2001, 79, 1541-1545].

In summary, strategies disclosed in prior art for the production of 2,6-diisopropylphenol (Propofol) predominantly involve synthesis starting from phenol or by using protected 4-position of phenol like, 4-hydroxybenzoic acid, 4-chlorophenol (references: Baltalksne, A. E.; Zitsmanis, A. H. SU 443019, 1974. Jain, K. P., Edaki, D. U., Minhas H. S., Minhas G. S. WO/2011/161687 A1, 2011. Wu, M. U.S. Pat. No. 4,391,998, 1983. Tsutsumi, S.; Yoshizawa, T.; Koyama, K. Nippon Kagaku Zasshi 1956, 77, 737-738. Paiocchi, M. U.S. Pat. No. 5,589,598, 1996. Nieminen, K., Essen, P. U.S. Pat. No. 5,175,376, 1992. Keller, S., Schlegel, J. WO/2012/152665 A1, 2012). Processes described in the literature generally propose purification of crude 2,6-diisopropylphenol by 'high vacuum distillation or molecular distillation'.

The phenols are susceptible to oxidation, formation of polymeric and color impurities. There are processes where repeated vacuum distillation has been carried out to obtain desired purity of product. Sometimes, to reduce the oxidized and colored impurities, reduction of impurities by catalytic hydrogenation is also used.

Propofol that does not meet Pharmaceutical grade may be manufactured by several processes generally known to persons of skill in the art and described in prior art, but purification of Propofol to consistently achieve high purity required for the injectable drug substance using an economical and industrial process remains a challenge.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure may be included in the examples summarized here.

Disclosed herein is a method for the purification of 2,6-dialkylphenols, specifically of 2,6-diisopropylphenol commonly known as Propofol that is therapeutically used as an anaesthetic in medical practice. An embodiment of the present invention a method of manufacturing a substantially pure Propofol comprises steam distillation.

In one representative embodiment, crude Propofol layer is added to purified water in a reactor and slowly heated to boiling to co-distil Pure Propofol along with water under normal atmospheric pressure. In another representative embodiment, crude Propofol liquid layer is charged into a reactor with steam distillation arrangement, like steam purging dip tube, column, heat exchanger and receivers. Pure steam is purged in the reactor at controlled pressure to co-distil Pure Propofol with water. In yet another representative embodiment, steam distillation may be performed under vacuum and/or in an inert atmosphere comprising inert gases such as nitrogen, argon or mixtures thereof.

DESCRIPTION OF THE INVENTION

Embodiments described herein provide the user a novel method to obtain Pure Propofol. The term Pure Propofol as used herein refers to pharmaceutically pure. In one embodiment, Propofol is more than 99.90% pure by HPLC (area normalization). The term 'Crude Propofol' as used herein refers to Propofol having a purity of less than 99.90% by HPLC (area normalization). Crude Propofol may comprise phenolic or other substances formed during manufacturing process including, without limitations, process or degradation impurities.

In one embodiment, the process of steam distillation comprises distillation of temperature sensitive product that is steam volatile and is performed under normal atmospheric temperature and pressure. In another embodiment, steam distillation is performed under vacuum conditions. In yet another embodiment, steam distillation is carried out by purging live steam in a mixture of Crude Propofol to be distilled along with water,-then separating the two phases to collect the Pure Propofol and discarding water or by co-distilling the volatile product with boiling water and separating the two phases to collect the Pure Propofol and discarding water.

The phenolic impurities that may be present in Crude Propofol manufactured by processes generally known to persons of skill in the art are listed in Table 01. These phenolic impurities listed in Table 01 can form sodium salt under alkaline condition and thus, do not distill with steam or boiling water. On the other hand, 2,6-diisopropylphenol does not form sodium salt under alkaline conditions and does distill with steam or boiling water. Thus, during steam distillation of Crude Propofol, only 2,6-disiopropylpropylphenol can be distilled as a steam volatile product, either by using steam or by boiling it with water, because it does not form sodium salt under the operating conditions. Furthermore, steam being inert, protects Pure Propofol from oxidation.

TABLE 01
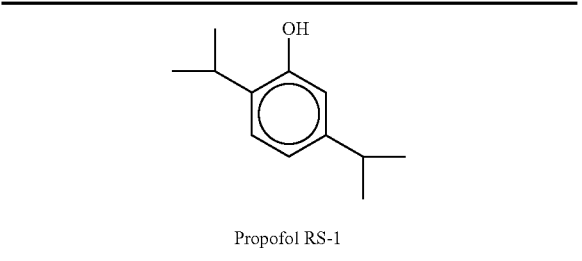
Propofol RS-1
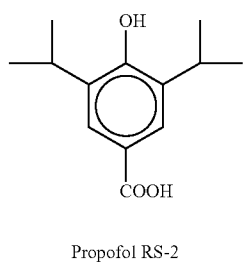
Propofol RS-2
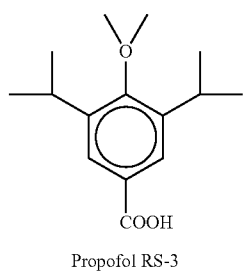
Propofol RS-3
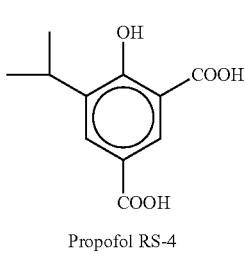
Propofol RS-4
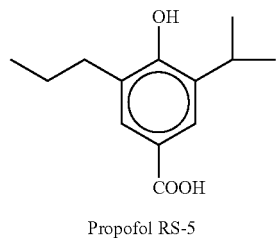
Propofol RS-5
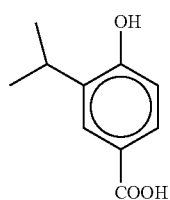
Propofol RS-6
TABLE 01-continued
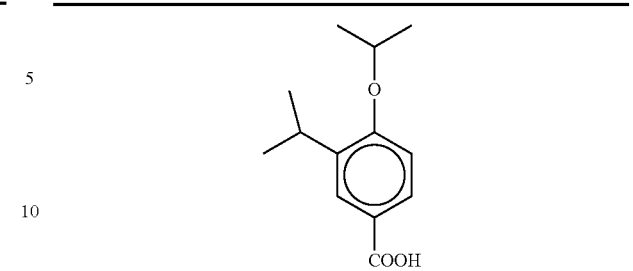
Propofol RS-7
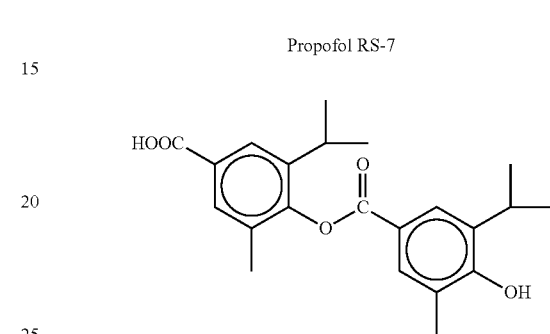
Propofol RS-8
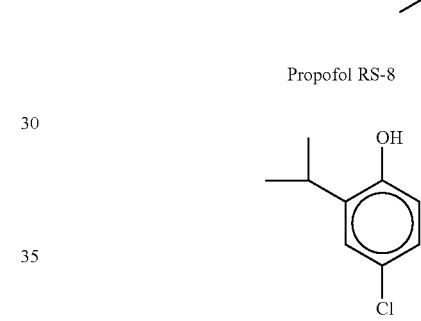
Propofol RS 9
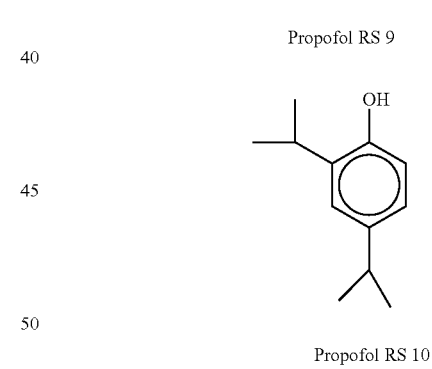
Propofol RS 10
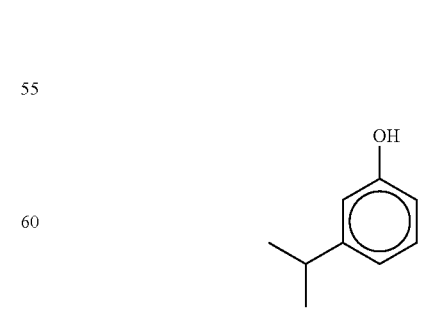
Propofol RS 11

TABLE 01-continued

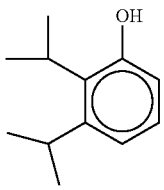

Propofol RS 12

Most of the impurities present in Crude Propofol are phenolic derivatives that are potentially steam volatile. The idea is to convert the impurities into compounds that are not steam volatile and simultaneously maintain the steam volatility of Propofol. In one embodiment, the reactive properties of Propofol are utilized to distinguish and separate Pure Propofol from the impurities present in Crude Propofol. The advantage in the case of 2,6-diisopropylphenol is that it does not easily form sodium (or potassium) salt with general process of treatment with alkali. It requires sodium methoxide to form sodium salt. Thus, in the presence of alkali such as sodium hydroxide or potassium hydroxide, 2,6-diisopropylphenol remains as phenolic derivative, and is steam distillable. It was surprisingly found that when crude 2,6-diisopropyl phenol containing phenolic impurities is in the presence of aqueous alkali, 2,6-diisopropylphenol distils along with steam or water. All other unwanted phenolic impurities form sodium salt, and thus do not distil with steam. Additional advantage using an alkali is that Propofol remains as an oily liquid, and thus is easy to separate from the aqueous layer and alkali soluble impurities. In another embodiment, Propofol that is substantially pure may be obtained by using phase separation techniques such as decantation to separate oily layer of Propofol from the aqueous layer and alkali soluble impurities.

One embodiment of the present invention relates to the manufacture of pharmaceutical injectable grade Propofol (FIG. 01; formula 01), with a purity of more than 99.9% using parabens, preferably methyl paraben shown in FIG. 02; formula 02-a, as starting material. Methyl paraben is one of the excipients that is routinely used in the Pharmaceutical preparation and thus available as a high purity product.

An embodiment of the process to manufacture Propofol is depicted in a reaction scheme in FIG. 1.

The process consists of standard 'Friedel-Crafts Alkylation' reaction using sulfuric acid as Lewis acid. Friedel-Crafts Alkylation reaction with isopropanol as an alkylating agent is carried out in the presence of sulfuric acid, water is released as a by-product.

The product 2,6-diisopropyl-4-hydroxy benzoic acid methyl ester (3,5-diisopropylmethylbenzoare) that is formed, gets hydrolysed in-situ to yield 3,5-diisopropyl-4-hydroxy benzoic acid.

After complete alkylation and hydrolysis of methyl ester (in-situ hydrolysis), the cooled reaction mixture is quenched, in chilled water or preferably in a mixture of toluene and water. The product 3,5-diisopropyl-4-hydroxy benzoic acid that is formed is extracted in toluene and toluene layer is separated. The toluene is then recovered by distillation and the residue, 3,5-diisopropyl-4-hydroxy benzoic acid is used for the next step of decarboxylation.

Decarboxylation is carried out using ethylene glycol at around 140° C. Once decarboxylation is complete, ethylene glycol dissolved in water is separated from product layer. The liquid crude Propofol is distilled by passing live steam or by distilling water, where Propofol distils leaving behind the phenolic impurities.

The water layer is separated from the distilled Propofol (Propofol has slight solubility in water) and it is made anhydrous either by extracting it in solvents like hexane, toluene or similar aromatics. The solvent, if used for extracting Pure Propofol, is then distilled under inert environment and final traces are eliminated by applying vacuum and degassing. Propofol thus obtained has a purity of more than 99.90%, and meets the residual solvent as well as related substance pharmacopoeial limit.

FIG. 2 (a through d) shows a block diagram of an embodiment of the manufacturing process inclusive of the steps of Friedel Craft's alkylation, decarboxylation followed by steam distillation/co-distillation to obtain high purity Propofol. This block diagram depicts an embodiment of a process of the present invention, and any variation followed by a person skilled in the art is not be interpreted as out of the scope of the process of the present invention.

Examples of the process used during a scale-up batch manufacture are given below and do not limit the scope of the invention. The particular examples described are not provided to limit the invention, but to illustrate it.

Example 1

Commercially available concentrated sulfuric acid (30 Kg) was diluted with water (2.26 Kg) at low temperature (0-15° C.). Methyl 4-hydroxybenzoate (5 Kg 32.79 mol.) was added to this diluted sulfuric acid at 5 to 10° C. with stirring. After complete addition, isopropyl alcohol (5.9 Kg 98.16 mol.) was gradually added to the reaction content, controlling the temperature at 0-15° C. The reaction mixture was then heated at 60-70° C. and continued to complete di-isopropylation and ester hydrolysis to yield methyl-4-hydroxybenzoate. The conversion was checked on TLC or by HPLC for the complete conversion of methyl-4 hydroxybenzoate to 3,5-Diisopropyl 4-hydroxybenzoic acid.

The reaction contents were cooled at room temperature and carefully charged into a stirred, precooled mixture of water (50 L) and Toluene (40 L) at (0 to 5° C.). The mixture was stirred and maintained below 15° C. for about 30 to 60 minutes.

The content was then heated at 25 to 30° C., stirred for 30 min., allowed to settle into two layers. The water layer was extracted again with toluene and discarded. The toluene layers, containing the product 3, 5-Diisopropyl 4-hydroxybenzoic acid, were combined and extracted with about 25 L of 10% NaOH. The aqueous layer containing the sodium salt of 3, 5-Di-isopropyl 4-hydroxybenzoic acid was acidified with concentrated HCl (about 9 Kg) to precipitate 3, 5-Diisopropyl 4-hydroxybenzoic acid, filtered, and washed with water (about 50 L) to yield 3,5-diisopropyl 4-hydroxybenzoic acid (about 45-60%)

To the mixture of 3, 5-diisopropyl 4-hydroxybenzoic acid (3 Kg, 13.5 mol.) in ethylene glycol (5.0 Kg, 80.55 mol.) was added sodium hydroxide (1.25 Kg, 31.25 mol.) for decarboxylation. The reaction mixture was heated at 145±5° C. till completion of decarboxylation by monitoring using TLC or HPLC (or solubility in bicarbonate of precipitated product). After complete decarboxylation, the reaction mixture was cooled at 40 to 45° C., under nitrogen environment and diluted with water (about 15 L) and allowed to settle. The oily product layer was separated and washed with water (6 L) to isolate crude Propofol (i.e., 2,6-diisopropyl phenol) and stored under nitrogen. The isolated volatile Crude Propofol (along with carry over ppm ethylene glycol and NaOH) was then subjected to steam distillation purification process as described below.

The Crude Propofol is purified by using one of the steam distillation processes as described below.

The Crude Propofol layer is added to purified water in a reactor (preferably glass lined reactor), and slowly heated to boiling to co-distil Pure Propofol along with water under normal atmospheric pressure and the high volatile initial fraction is isolated first. The biphasic layers of main distillate, are separated and the liquid layer of Propofol is treated with dehydrating agent to absorb dissolved moisture in Pure Propofol under nitrogen or argon. The transparent Pure Propofol liquid layer is then filtered through ultrafine Micron filter (0.45 and 0.2 micron) under nitrogen (or argon) pressure and isolated in controlled environment to obtain pharmaceutical injectable grade Pure Propofol of more than 99.90% purity.

The Crude Propofol liquid layer is charged into a reactor with steam distillation arrangement, like steam purging dip tube, column, heat exchanger and receivers. Pure steam is purged in the reactor at controlled pressure to co-distil Pure Propofol with water. The layers are allowed settle and water layer is kept aside for recirculation. The transparent Pure Propofol transparent liquid layer is then filtered through ultrafine Micron filter (0.45 and 0.2 micron) under nitrogen (or argon) pressure and isolated in controlled environment to obtain pharmaceutical injectable grade Pure Propofol of more than 99.90% purity.

The Crude Propofol layer is added to purified water in a reactor (preferably glass lined or Hastelloy reactor) and slowly heated at boiling to co-distil Pure Propofol along with water under mild vacuum. The biphasic layers are separated and the liquid layer of Propofol is treated with dehydrating agent to absorb dissolved moisture in Pure Propofol under nitrogen (or argon). The transparent Pure Propofol liquid layer is then filtered through ultrafine Micron filter (0.45 and 0.2 micron) under nitrogen (or argon) pressure and isolated in controlled environment to obtain pharmaceutical injectable grade Pure Propofol of more than 99.90% purity.

The Crude Propofol layer is added to reactor containing purified water and 0.1 to 1% antioxidant and 0.1 to 0.5% sodium hydroxide and slowly heated to boiling to co-distil Pure Propofol along with water. The biphasic layers are separated and the liquid layer of Propofol is treated or passed through column packed with dehydrating agent to absorb dissolved moisture in Pure Propofol. The transparent Pure Propofol liquid layer is then filtered through ultrafine Micron filter (0.45 and 0.2 micron) under nitrogen (or argon) pressure and isolated in controlled environment to obtain pharmaceutical injectable grade Pure Propofol of more than 99.90% purity.

The crude Propofol liquid layer is treated with preferably neutral or basic activated carbon (about 2-5%) and filtered under nitrogen. The filtered liquid is collected, under nitrogen, in distillation reactor containing purified water is slowly heated to boiling to co-distil Pure Propofol along with water under normal pressure or mild vacuum. The co-distilled biphasic layers are separated and the liquid layer of Propofol, is treated under nitrogen, with or passed through column packed with dehydrating agent to absorb dissolved moisture trapped in Pure Propofol. The transparent Pure Propofol liquid layer is then filtered through ultrafine Micron filter (0.45 and 0.2 micron) under nitrogen (or argon) pressure and isolated in controlled environment to obtain pharmaceutical injectable grade Pure Propofol of more than 99.90% purity.

Example No. 2

Friedel-Crafts reaction was performed as described in Example 1. Decarboxylation was performed by using KOH instead of NaOH by following the same procedure as described in Example 1.

Example No. 3

Decarboxylation was performed as per operations described in Example 1. After complete decarboxylation, the reaction mixture was cooled at 40 to 45° C., under nitrogen environment and diluted with water (about 15 L) The biphasic mixture subjected to steam distillation by any of the purification methods described in Example 1.

Example No. 4

Friedel-Crafts reaction was performed as described in Example 1. The reaction contents were cooled at room temperature and carefully charged at 0 to 5° C. into a sodium hydroxide solution to basic pH at stirred. The aqueous alkaline solution was extracted twice with toluene or hexane. The aqueous layer was acidified with HCl to precipitate 3, 5-diisopropyl-4-hydroxybenzoic acid. The wet product was washed with water, dried and decarboxylated using sodium hydroxide in ethylene glycol as solvent at 145±5° C. The reaction contents were cooled to room temperature, diluted with water and acidified and then Crude Propofol was extracted twice in toluene. The toluene layer was washed with water, bicarbonate and with water then distilled to obtain crude oily layer of Propofol (>99% pure). This Crude Propofol was then purified by using purification steam distillation by any of the purification methods described in Example 1.

Example 5

Continuous steam distillation of crude Propofol by purging pure steam. Continuous steam distillation of Crude Propofol was carried out using a feed pump for feeding liquid Crude Propofol (prepared by one of the processes described in this application or other literature) to the steam distillation system connected to a pure steam generator. Steam at 1-10 kg pressure was purged in the steam distillation system at controlled rate and the co-distilled Pure Propofol with water was cooled using heat exchanger and continuous separator. The residue was discharged from bottom valve at defined time intervals. The water layer was recycled to steam generator and Pure Propofol was dehydrated, filtered and collected in controlled environment as described in Example 1.

It will be appreciated that several of the above-disclosed and other features and functions, or alternatives or varieties thereof, may be desirably combined into many other different processes or applications. Also, that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide a thorough understanding of the embodiments. It will be apparent however, to one skilled in the art, that one or more other embodiments may be practiced without some of these specific details. The particular embodiments described are not provided to limit the invention, but to illustrate it. The scope of the invention is not to be determined by the specific examples provided above. In other instances, well-known structures and processes have been shown in block diagram form or without detail in order to avoid obscuring the understanding of the description.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments.

The invention claimed is:

1. A process for manufacturing a substantially pure Propofol from a Crude Propofol, said Crude Propofol comprising Propofol and phenolic impurities, said process comprising:
   i. adding an aqueous alkali to the Crude Propofol thereby forming a mixture comprising the Crude Propofol and the aqueous alkali;
   ii. doing a steam-distillation and/or co-distillation of the mixture with boiling water at normal atmospheric pressure to provide a bi-phasic distillate comprising an oily liquid layer of distilled Propofol and an aqueous layer; and
   iii. separating the oily liquid layer of the distilled Propofol;
   wherein the process comprises at least decarboxylation to provide the Crude Propofol;
   wherein the process excludes the presence of an inert atmosphere during the addition of the alkali to the crude Propofol;
   wherein the phenolic impurities in the Crude Propofol form alkali salts under alkaline condition and the alkali salts of the phenolic impurities do not distill with a-steam or with boiling water;
   wherein Propofol in the Crude Propofol does not form the alkali salt under alkaline condition and Propofol distills with the steam or with boiling water to provide the distilled Propofol; and
   wherein, during distillation, the protects the steam distilled Propofol from oxidation.

2. The process of claim 1, wherein the substantially pure Propofol has a purity of more than 99.90%.

3. The process of claim 1, further comprising filtering the oily liquid layer of the distilled Propofol through an ultra-fine micron filter.

4. The process of claim 3, wherein the ultra-fine micron filter is selected from a group including 0.45 micron and 0.2 micron.

5. The process of claim 1, wherein the alkali is selected from a group including sodium hydroxide and potassium hydroxide and the alkali salts comprise a sodium and/or a potassium salt.

6. The process of claim 1, wherein the mixture further comprises an antioxidant.

7. The process of claim 1, further comprising separating the aqueous layer from the oily liquid layer of the distilled Propofol using a phase separation technique and then removing any remaining water in the oily liquid layer using a dehydrating agent to obtain the substantially pure Propofol.

8. The process of claim 1, further comprising extracting the distilled Propofol in a low-boiling solvent in which Propofol is soluble, and subsequently distilling the low-boiling solvent wherein the low-boiling solvent forms an azeotrope with water thereby leaving behind the substantially pure Propofol.

9. The process of claim 8, wherein distilling the low-boiling solvent removes traces of the low-boiling solvent or water and is performed under vacuum.

10. The process of claim 1, wherein at least methyl paraben is used as a starting material for preparation of the Crude Propofol.

11. The process of claim 1, wherein 4-hydroxy-alkylbenzoate is used as a starting material for preparation of the Crude Propofol.

12. The process of claim 11, wherein 4-hydroxy-alkylbenzoate is firstly converted into 3,5-diisopropyl-4-hydroxy-alkylbenzoate, and further comprises hydrolysis and decarboxylation to provide the Crude Propofol.

13. The process of claim 12, wherein the Crude Propofol comprises Propofol, the phenolic impurities and ethylene glycol.

14. A process for manufacturing a substantially pure Propofol from a Crude Propofol, said Crude Propofol comprising Propofol and phenolic impurities, said process comprising:
   i. adding an alkali to the Crude Propofol thereby forming a mixture comprising the Crude Propofol and the alkali;
   ii. doing a steam-distillation and/or co-distillation of the mixture with boiling water at normal atmospheric pressure to provide a bi-phasic distillate comprising an oily liquid layer of a steam-distilled Propofol and an aqueous layer;
   iii. doing phase separation of the bi-phasic distillate wherein the oily liquid layer of the distilled Propofol is separated from the aqueous layer using a phase separation technique;
   iv. removing any remaining water in the oily liquid layer of the distilled Propofol using a dehydrating agent; and
   v. filtering the oily liquid layer of the distilled Propofol through an ultra-fine micron filter;
   wherein the process comprises at least decarboxylation to provide the Crude Propofol;
   wherein the process excludes the presence of an inert atmosphere during the addition of the alkali to the crude Propofol;
   wherein the phenolic impurities in the Crude Propofol form alkali salts under alkaline condition and the phenolic impurities do not distil with a steam;
   wherein Propofol in the Crude Propofol does not form the alkali salt under alkaline condition and Propofol distils with the steam to provide the distilled Propofol; and
   wherein, during distillation, the steam protects the distilled Propofol from oxidation.

15. The process of claim 14, wherein the substantially pure Propofol has a purity of more than 99.90%.

16. The process of claim 14, wherein the ultra-fine micron filter selected from a group including 0.45 micron and 0.2 micron.

17. The process of claim 14, wherein the alkali is selected from a group including sodium hydroxide and potassium hydroxide and the alkali salts comprise a sodium and/or a potassium salt.

18. The process of claim 14, wherein 4-hydroxy-alkyl-benzoate is used as a starting material for preparation of the Crude Propofol.

19. The process of claim 18, wherein 4-hydroxy-alkyl-benzoate is firstly converted into 3,5-diisopropyl-4-hydroxy-alkylbenzoate, and further comprises hydrolysis and decarboxylation to provide the Crude Propofol.

* * * * *